(12) United States Patent
Gustafsson et al.

(10) Patent No.: US 6,443,935 B1
(45) Date of Patent: *Sep. 3, 2002

(54) METHOD AND DEVICES FOR LAYING A THREAD ON A SUBSTRATE IN A ZIGZAG PATTERN

(75) Inventors: Anders Gustafsson, Billdal; Urban Widlund, Mölnlycke, both of (SE)

(73) Assignee: SCA Molnlycke AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/875,736

(22) PCT Filed: Feb. 1, 1996

(86) PCT No.: PCT/SE96/00116

§ 371 (c)(1),
(2), (4) Date: Sep. 23, 1997

(87) PCT Pub. No.: WO96/23464

PCT Pub. Date: Aug. 8, 1996

(30) Foreign Application Priority Data

Feb. 2, 1995 (SE) .............................. 9500384

(51) Int. Cl.⁷ ........................... A61F 13/15; A61F 13/20
(52) U.S. Cl. ........................... 604/385.26; 604/385.29; 604/385.3; 26/90; 156/161; 156/177; 156/178; 156/229; 156/495; 156/496
(58) Field of Search ................. 26/87, 88, 90; 156/161, 163, 164, 177, 178, 229, 494, 495, 496; 604/385.2, 385.1, 365–366, 393–396, 348, 385.23–385.3

(56) References Cited

U.S. PATENT DOCUMENTS

| | | | | |
|---|---|---|---|---|
| 3,560,292 A | * | 2/1971 | Butter | 156/229 |
| 4,718,901 A | * | 1/1988 | Singheimer | 604/385.2 |
| 4,925,520 A | | 5/1990 | Beaudoin et al. | |
| 4,946,539 A | * | 8/1990 | Ales et al. | 156/495 |
| 5,000,806 A | * | 3/1991 | Merkatoris et al. | 156/494 |
| 5,221,390 A | * | 6/1993 | Persson et al. | 156/164 |
| 5,545,285 A | | 8/1996 | Johnson | |

FOREIGN PATENT DOCUMENTS

| | | | | |
|---|---|---|---|---|
| DE | 2 144 694 | * | 3/1972 | 156/178 |
| EP | 0 338 662 | | 10/1989 | |
| EP | 0 443 244 | | 8/1991 | |
| EP | 0 626 160 | * | 11/1994 | 604/385.2 |
| ES | 2 022 026 | * | 11/1991 | |
| GB | 2 267 024 | | 11/1993 | |
| GB | 2 276 529 | | 10/1994 | |
| JP | 4 220 341 | * | 8/1992 | 156/229 |
| SE | 209 771 | | 12/1966 | |

* cited by examiner

Primary Examiner—Aaron J. Lewis
Assistant Examiner—K. M. Reichle
(74) Attorney, Agent, or Firm—Young & Thompson (57) ABSTRACT

In a method and device for applying a thread to a moving substrate, a thread is continuously dispensed to a pick-up point adjacent to the point of contact of two rotating wheels (2, 3) that are inclined towards each other. The peripheries of the wheels have fingers (7) which hook the thread and move it to one side or the other as the wheels rotate, and then deposit the thread extended between the fingers 180° from the pick-up point. Long spaces between the fingers (7) on one wheel or the other make it possible to lay the thread longitudinally (8b) or in a long diagonal line instead of merely in a lateral zigzag pattern. The method and device may be used to make an absorbent article, such as a diaper.

2 Claims, 7 Drawing Sheets

METHOD AND DEVICES FOR LAYING A THREAD ON A SUBSTRATE IN A ZIGZAG PATTERN

BACKGROUND OF THE INVENTION

The present invention relates to a method for applying a thread onto a relatively moving substrate. The present invention also relates to devices for carrying out the method.

Such a method and device for applying a thread onto a relatively moving substrate is described in Swedish Patent No. 209 771. It describes how lengths of thread can be laid substantially transversely over longitudinal threads moving thereunder to thereby form a net elastic web. Two wheels inclined towards each other above the substrate of longitudinal threads almost touch at the top. Each of the wheels is provided on its periphery with uniformly spaced fingers which alternatingly hook a thread dispensed centrally from a spool to said point of contact between the inclined wheels, as the wheels rotate. The alternating hooks thus move away from each other as they are moved with the periphery of their respective wheels, thereby gradually extending the thread, somewhat in the manner of a "cat's cradle", in a zigzag pattern from one wheel to the other, reaching its broadest extent directly above the substrate and diametrically opposite to the pick-up point of contact between the two wheels. In the method and device shown in this Swedish patent specification, the transversely extended threads, upon reaching their point of greatest extension, are cut by a knife and glued to the longitudinal threads.

By this known method and device however with uniformly spaced fingers and where the threads are cut off in transverse lengths, only a transverse pattern can be created with the thread. In the manufacture of elastic pants products such as pants diapers cut end-to-end from a web, it is necessary to lay elastic threads transversely in the waist area for example, and longitudinally to elasticize the leg openings for example. Up to now this has involved a number of different separate process procedures making the method complex, and thus costly and/or prone to error, and different threads which have to be glued separately, at least at their ends, and this can give rise to a number of loose ends in the product.

SUMMARY OF THE INVENTION

All of these problems are solved by the method described herein. In this way it is possible to apply a single or several parallel elastic threads continuously along a pants diaper web of indefinite length, thus providing both transverse elasticity in the waist portion and sealing elasticity around one or more leg openings as well as longitudinal elasticity over the crotch portion, as will be evident from the detailed description of the present invention.

One inventive device for carrying out the method according to the invention removes certain of the projecting elements from one or both of the wheels enabling the device to lay down the thread continuously with both transverse zigzag portions and entirely longitudinal and/or inclined longitudinal portions.

A second inventive device for carrying out the method according to the invention includes projections that can be shaped so that certain of them release the thread from engagement, thus creating the same pattern as with the device described above but with a different elasticity in the longitudinal portions.

According to one particularly advantageous embodiment of the invention, the projecting elements or fingers are mounted externally on belts running on the inclined wheels, which in this case are pulleys. The belts run on the inclined pulleys from the pick-up point to the points diametrically opposite therefrom. The belts leave the front inclined pulleys there however, keeping the thread in its extended zigzag/longitudinal pattern. The thread can either be pressed by suitable means, a roller for example, off the projections into application against the substrate or the belts can be twisted inwards by virtue of a second pair of pulleys being vertically aligned or oppositely inclined to the first pair of wheels/pulleys, or the two methods can be combined. According to a preferred practical embodiment, two pairs of inclined wheels in spaced longitudinal and transverse relationship transfer the thread, preserving its zigzag/longitudinal pattern, to a conveyor belt carrying fingers or projections running in two parallel rows.

The method according to the present invention can be used with particular advantage in, but is not limited to, the manufacture of disposable absorbent articles such as diapers, pant diapers, sanitary briefs, incontinence shields etc.

BRIEF DESCRIPTION OF THE DRAWINGS

The invention will now be described in more detail below with reference to several examples shown in the accompanying drawings of which.

DESCRIPTION OF THE PREFERRED EMBODIMENTS

Figure 1:
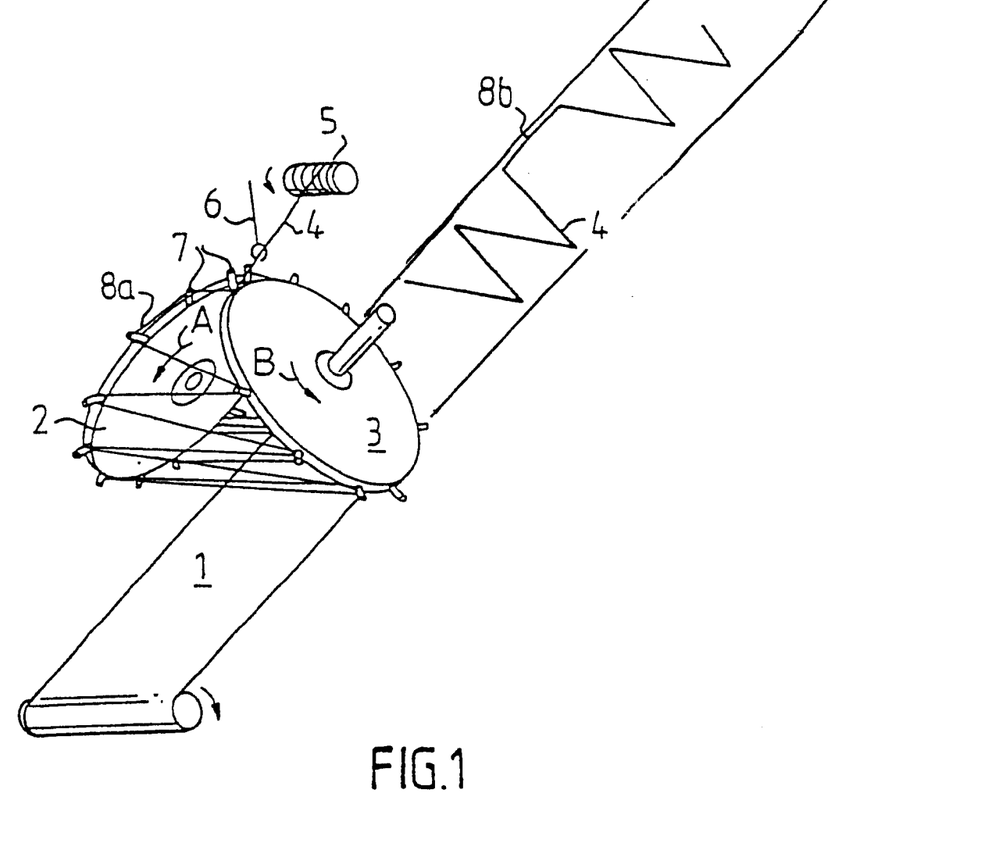
FIG. 1 shows the principle of the invention with reference to a schematic representation in perspective of an embodiment of the device.

As can be seen in FIG. 1, a substrate web 1, which can be the cohesive pants layer of a pants diaper for example, moves beneath two rotating wheels 2, 3. These wheels 2, 3 are inclined towards each other and almost touch each other at their uppermost points. A thread 4, which in this case can be an elastic cotton spun rubber thread or a LYCRA elastic thread is dispensed from a spool 5 and runs through a thread guide 6 to the point of contact between the two wheels 2, 3. There the thread is hooked to one side or the other by the projecting elements or fingers 7 distributed around the outer periphery of each wheel and which cross each other at the point of contact. To produce a zigzag pattern the projecting elements or fingers 7 are arranged evenly spaced on converging portions of the two wheels alternatingly hooking the thread. As the wheels 2, 3 rotate, as indicated by the arrows A and B in the drawing, the respective fingers, with the thread hooked thereto will diverge, extending the thread between them in a broader and broader zigzag pattern, until reaching a lowermost point directly above the moving substrate web where means, a roller extending across the width of the substrate for example (not shown in FIG. 1), are arranged to push the thread out of engagement with the fingers 7 after having established adhesive contact with the substrate, thus laying out the thread in a zigzag pattern. It is also possible to provide the moving substrate with two rows of pins along the lateral margins thereof, to which the thread is transferred in its extended pattern to be subsequently sandwiched between two layers of non-woven fabric for example. Further embodiments are described below in connection with the discussion of FIGS. 7A, 7B, 8A, 8B.

Figure 2:
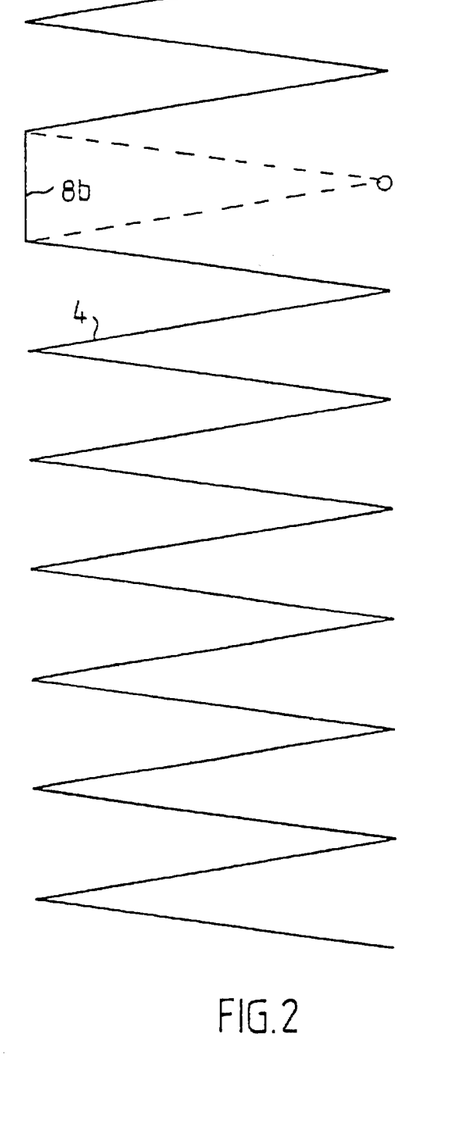
FIG. 2 shows in a solid line the thread pattern produced by the embodiment shown in FIG. 1, i.e. with one projecting element removed and in a dashed line thread extensions that do not occur due to removal of the one projecting element.
Figure 3:
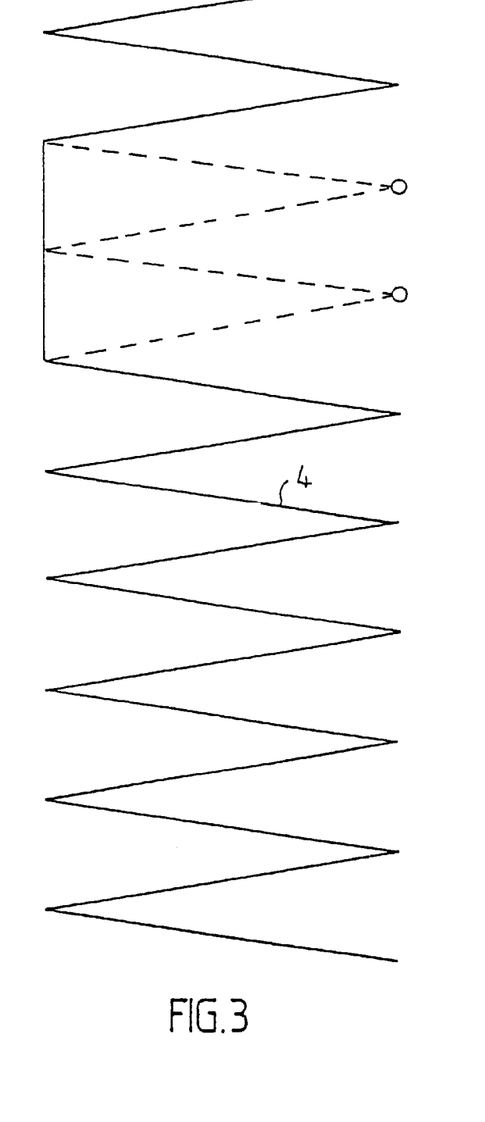
FIG. 3 shows in a solid line the thread pattern produced by an embodiment of the present invention (not shown) with two consecutive projecting elements left off one wheel and in a dashed line the thread extensions that do not occur due to removal of the two consecutive projecting elements.
Figure 4:
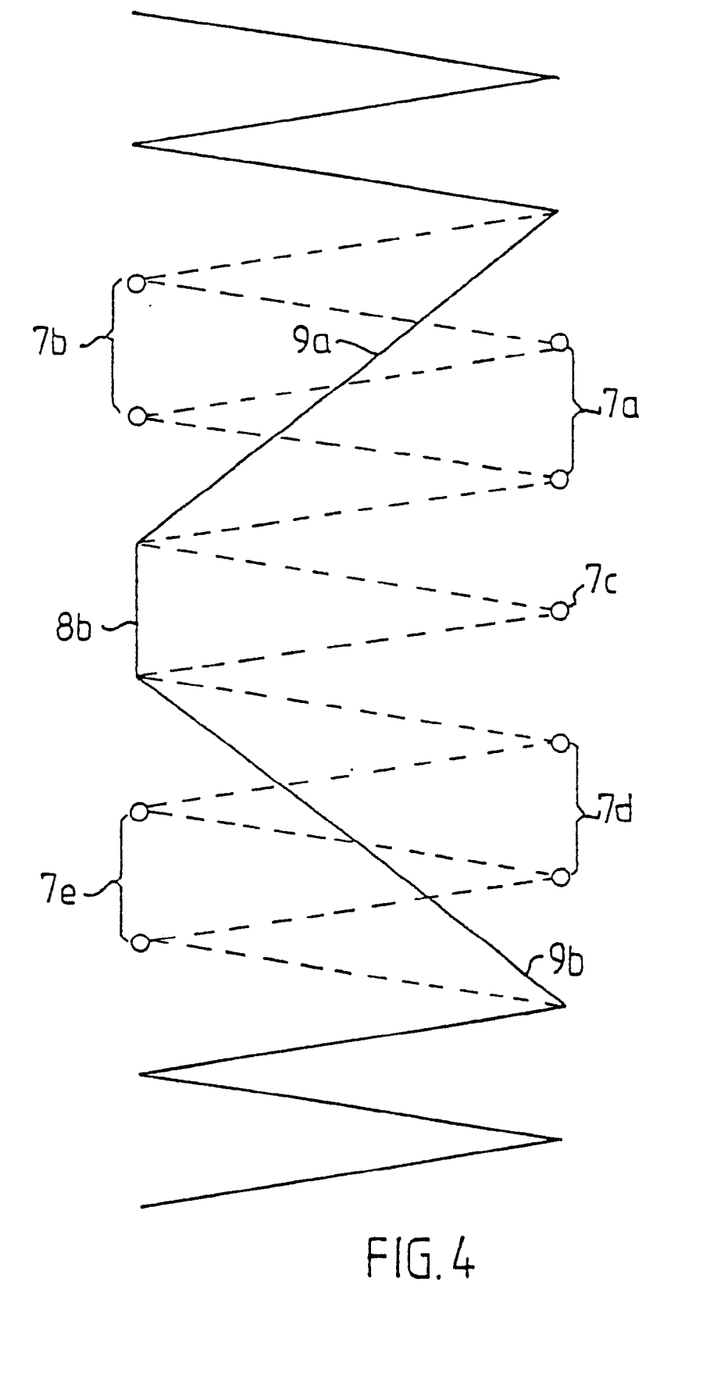
FIG. 4 shows in a solid line the thread pattern produced by an embodiment of the present invention (not shown) with several groups of consecutive projecting elements left off the two wheels and in a dashed line the thread extensions that do not occur due to removal of the several groups of consecutive projecting elements.
Figure 5:
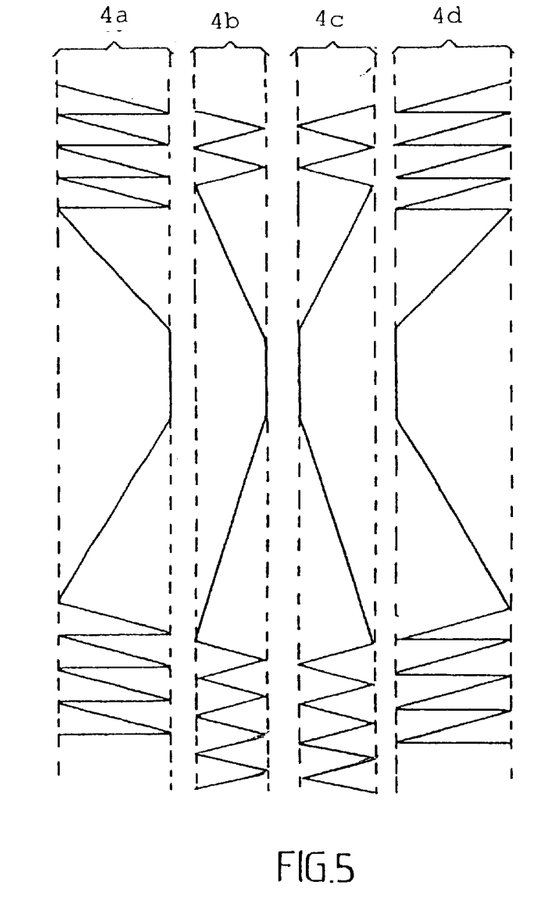
FIG. 5 shows the pattern which can be produced by using four parallel pairs of inclined wheels in accordance with the invention.
Figure 6:
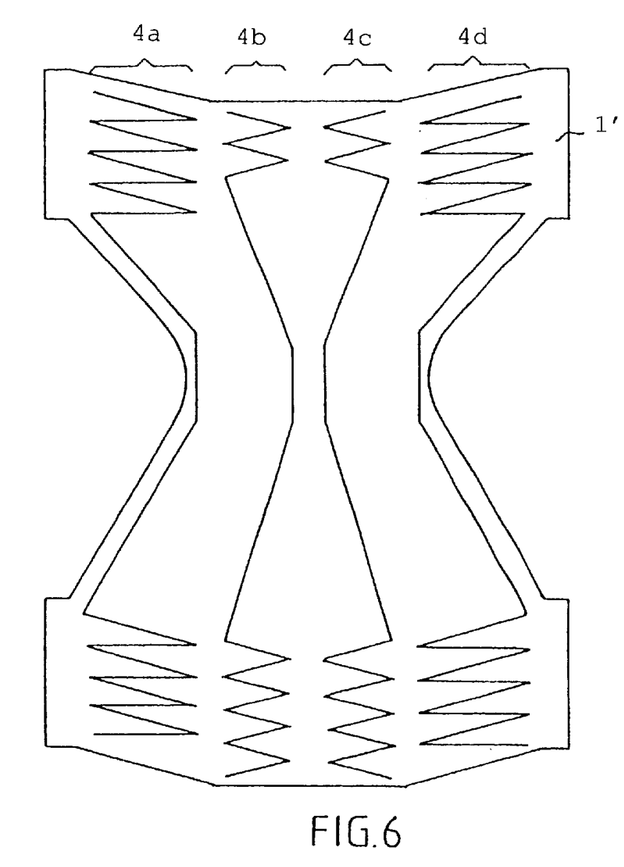
FIG. 6 shows an unfinished cut out diaper component with the pattern shown in FIG. 5.

Certain selected fingers or series of fingers may be left off one or the other wheel to lay the thread, longitudinally (as shown in FIG. 1, 2 and 3) or obliquely longitudinally as shown in FIGS. 4, 5 and 6, in addition to laying the thread in the basic zigzag pattern. In the example shown in FIG. 1 the thread is hooked and lain in the basic uniform zigzag pattern with the exception that one finger has been eliminated from the wheel 3, thus producing a longitudinal extension 8a of the thread, which is preserved in the longitudinal portion 8b of the thread in adhesive contact with the substrate 1.

This effect can of course be achieved in other ways; for example by designing certain of the fingers in such a way that they release the previously hooked thread before reaching adhesive contact with the substrate. This can alleviate problems with excessive transverse stretching of the thread.

The thread, which can be elastic, can also be laid between two layers of non-woven material which adhere to each other.

This has several advantages which will become evident from the explanation below.

FIG. 2 shows in a solid line the pattern of the thread produced by the device as configured in FIG. 1, with one finger being eliminated from one wheel, thus producing one longitudinal section 8b in the otherwise basic zigzag pattern of the thread 4. FIG. 3 shows the pattern produced when two fingers are eliminated from one wheel. FIG. 4 shows in a solid line pattern, which is very useful in the production of diapers and pants diapers as will become evident below. This pattern is produced by first eliminating a pair of fingers 7a, 7b from each wheel, thereby creating a diagonal portion 9a. The eliminated finger 7c produces a longitudinal section 8b, which is followed by a diagonal section 9b, oppositely oriented to the diagonal portion 9a, and which is produced by eliminating a pair of fingers 7d, 7e from each wheel. The dashed lines show the thread extensions that would have occurred if the fingers were not eliminated.

Four patterns of this type 4a, 4b, 4c, and 4d are laid out in parallel as shown in FIG. 5 and applied to an elasticized pants type diaper. To do this four pairs of inclined wheels are necessary. FIG. 6 shows an elasticized pants diaper component 1' in its unassembled state cut out of the substrate web with the four patterns 4a, 4b, 4c, 4d. The zigzag pattern areas at either end are transversely elasticized to provide an elastic waist. The two side columns 4a and 4d have the zigzag areas slanted to provide a concave edge surface to accomodate the protruding belly shape of the typical toddler, as described in Swedish Patent Application 9402867-7. The longitudinal crotch elastics provide leg sealing elastic and elastic pockets for urine and feces respectively and can be used in conjunction with the absorbent products described in SE 9404567-1.

Thus four parallel continuous threads provide lateral elasticity around the waist and longitudinal elasticity around the legs and in the crotch area. Each of the threads need only be severed at its ends thus making handling of the elastic very simple.

A further advantage is that if the threads are sandwiched between two layers of non-woven fabric, then each of the threads only needs to be bonded at its ends by gluing for example. The convoluted zigzag pattern will hold the rest of each thread in place since the non-woven fabrics are bonded to each other holding the zigzag pattern in place.

The method according to the invention can also be applied by using a device where the inclined wheels are pulleys and the projecting elements or fingers are fixed externally on belts running between said pulleys and second pulleys which are vertically oriented or even inclined oppositely to the first pair of pulleys. The fingers follow the periphery of the first inclined pulleys, functioning in exactly the same manner as the wheels with peripherally fixed fingers. The belts then leave the inclined pulleys when reaching the bottom directly above the substrate, keeping the thread extended in the desired pattern between the two belts. The threads can either be pressed by suitable means (e.g. a roller) off the fingers on the belts, and for example be sandwiched between two layers of non-woven fabric or the orientation of the second pulleys can be such that the thread slips naturally off the fingers as the belts are twisted.

Figure 7A:
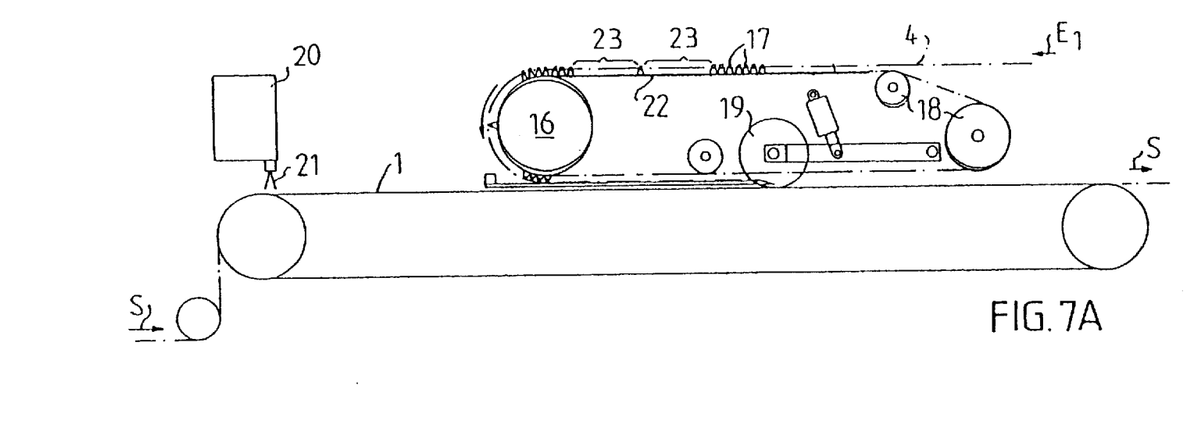
FIGS. 7A and 7B show a longitudinal view and an end view respectively of a schematic drawing of one practical embodiment of a device according to the invention for carrying out the method according to the invention.
Figure 7B:
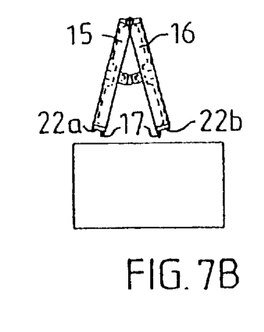

FIGS. 7A and 7B show one practical embodiment of the device according to the invention. A pair of inclined pulleys 15,16 carry belts 22a,b which run over opposite pulleys 18 to follow a path essentially parallel to the substrate 1. The belts 22a,b are provided with projections or fingers 17 spaced with appropriate longer gaps 23 to achieve the desired zigzag/longitudinal pattern. The thread 4, which in this case is an elastic thread, runs from a spool (not shown) in the direction of the arrow E1 along the entire upper run of the belts, where the fingers 17 carried by the belts 22a,b are held in crossed configuration with the thread running between them. Upon reaching the pulleys 15, 16, the belts 22a,b carrying the fingers 17 diverge creating the desired zigzag/longitudinal pattern which is preserved as the belts leave the pulleys and proceed along the lower run. A roller 19 running between the belts 22a,b along the lower run presses the thread in the zigzag/longitudinal pattern from the fingers 17 and onto the substrate 1 moving in direction S which has just been sprayed with glue 21 from a gluing unit 20, thus embedding the thread and preserving the desired zigzag/longitudinal pattern.

Figure 9:
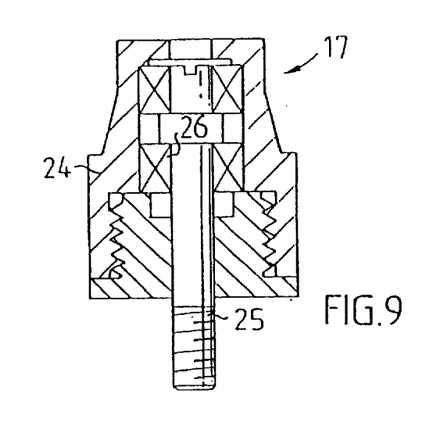
FIG. 9 shows a longitudinal section through one type of rotating finger cap which can be used.

In order to prevent friction between the thread 4 and the fingers 17 from causing excessive tension and breakage of the thread as the fingers diverge, each finger 17 is provided with a rotating cap 24 (See FIG. 9) which rotates freely on a finger pin 25 via either a journal bearing (not shown) or a rolling contact bearing 26.

Figures 8A, 8B:
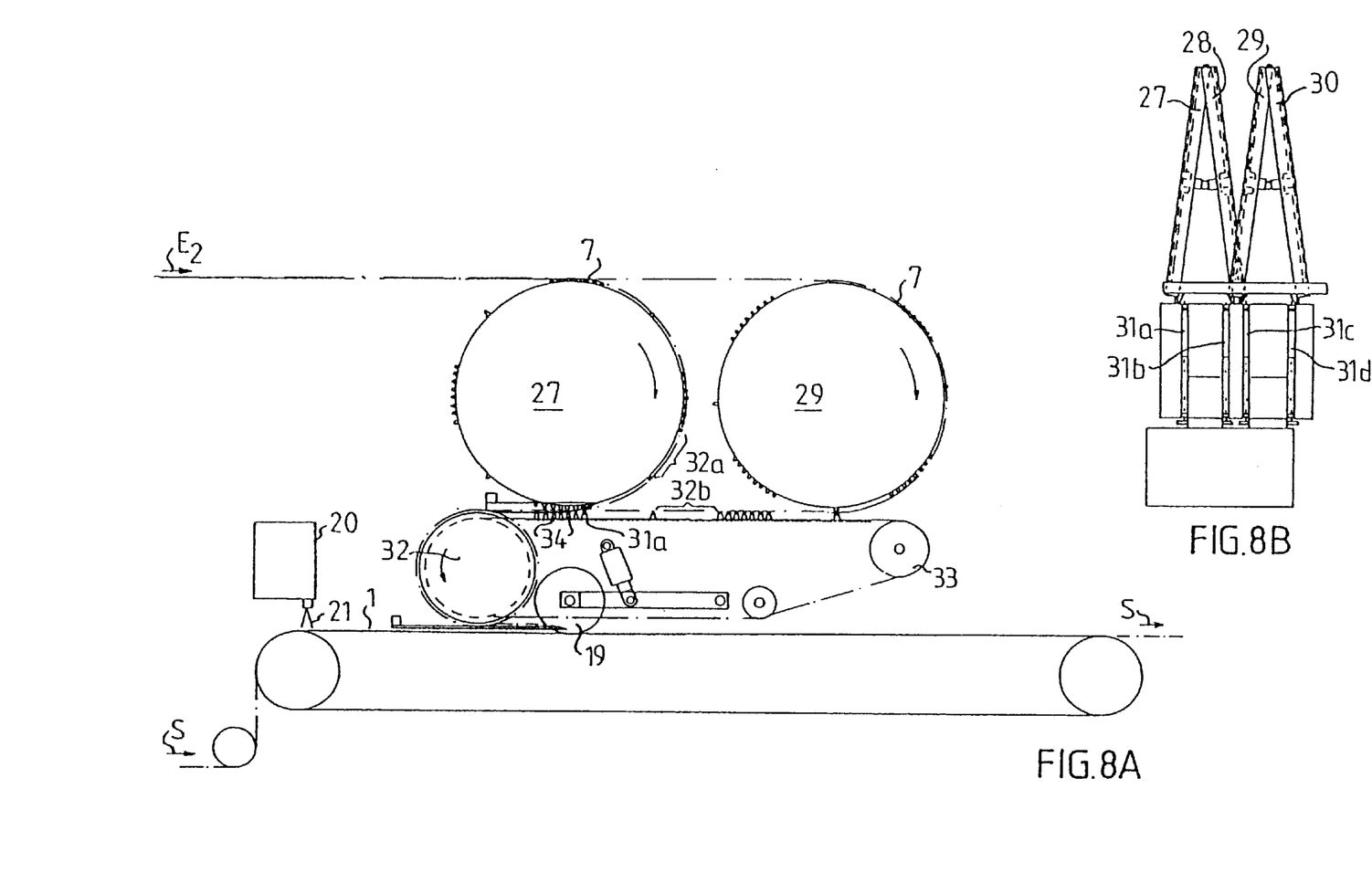
FIGS. 8A and 8B show a longitudinal view and an end view respectively of a schematic drawing of a second practical preferred embodiment of a device according to the invention for carrying out said method.

FIGS. 8a and 8b show in a longitudinal view and an end view respectively another preferred practical embodiment of the present invention using finger-equipped intermediate transfer belts 31a,b,c,d between two pairs of finger-equipped inclined wheels 27, 28 and 29, 30 and the moving substrate 1. The two pairs of inclined wheels 27, 28 and 29, 30 are spaced both longitudinally and laterally as can be seen in the drawing to provide two zigzag/longitudinal patterns on the substrate which are almost contiguous side-by-side. Each pair of inclined wheels receives between converging fingers a thread fed from one of two spools (not shown) in the direction $E_2$, whereupon the diverging fingers of the rotating wheels create the zigzag/longitudinal pattern in the manner described above. As the fingers reach the bottom of the rotating wheel, the thread is transferred, preserving the zigzag/longitudinal configuration of the thread, onto fingers 34 carried on belts 31a,b,c,d arranged in parallel relation to each other. There is one transfer belt 31a,b,c,d for each inclined wheel 27, 28, 29, 30. The thread after arriving at the substrate is then pressed into glue 21 which has been sprayed onto the substrate, in the same manner as was described above in conjunction with FIGS. 7A and 7B.

This arrangement with intermediate transfer belts prevents glue from penetrating into the finger cap bearings 26 (see FIG. 9) and preventing the finger caps 24 from rotating, and thereby giving rise to thread friction and thread breakage.

The intermediate transfer belts 31a,b,c,d, in contrast to the embodiment shown in FIG. 8a with longer gaps 32b corresponding to those 32a on the inclined wheels, can be provided a continuous tightly spaced series of fingers covering the entire belt. This eliminates the need for synchronization of the belts to the wheels while still preserving the original zigzag/longitudinal pattern produced by the inclined wheels 27, 28 and 29, 30. This also enables the pairs of wheels to be changed as needed to produce different patterns, without replacing or synchronizing the intermediate transfer belts 31a,b,c,d. Having a continuous tightly space series of fingers on each transfer belt also makes it possible to run belts at slightly different speeds so that one belt will advance during a complete cycle an intergral number of fingers in relation to the other belt in each pair of belts. This will enable one to achieve zigzag patterns which are skewed i.e. do not advance uniformly while moving from one side to the other (see patterns 4a and 4d in FIGS. 5 and 6) or are even retrograde from one side to the other.

It is also possible to arrange pairs of inclined wheels in direct series in order to superimpose different patterns on top of each other, for example a longitudinal pattern superimposed on a zigzag pattern to provide both longitudinal and transverse elasticity and/or strength.

Figure 10:
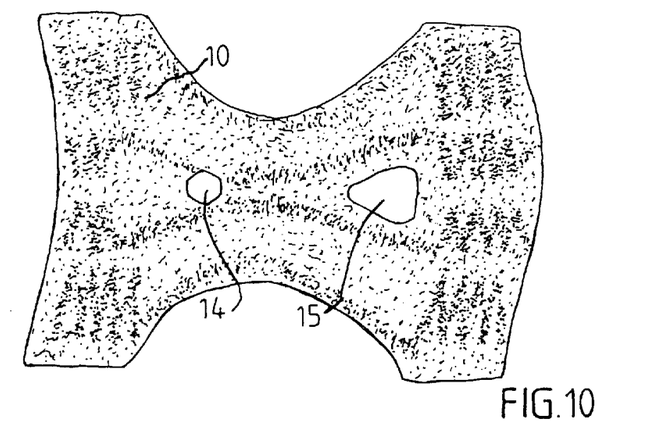
FIG. 10 is a pictorial representation of a pant diaper substrate with an elastic pattern (not shown) bonded to the substrate.

FIG. 10 shows a pant substrate 10 of a non-woven material and an elastic stretched as the elastic pattern described in connection with FIGS. 1–6. Pant substrate 10 may include a urine opening 14 and an anal opening 15.

Figure 11:
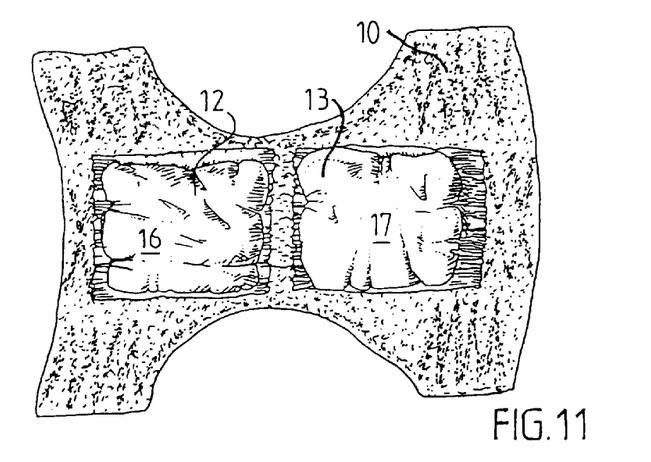
FIG. 11 is a pictorial representation of the pant diaper substrate of FIG. 10 with an elastic pattern (not shown) with an absorption unit fastened on the pant substrate.

FIG. 11 shows an absorption unit comprising two parts 12 and 13 where the first part 12 is arranged to cover the urine opening 14 in the pant substrate 10 and where the second part 13 is arranged to cover the anal opening 15. The absorption part 12, comprising an outer liquid impermeable cover 16, is fastened at its periphery against the pant substrate 10.

The space inside said cover 16 may be filled with an absorbent material, such as cellulosic fluff and/or absorbent gel.

The absorption part 13 for feces comprises an outer liquid impermeable cover 17 fastened at its periphery against the pant. The space inside the cover 17 is preferably empty as it intended to keep feces inside the cover.

Figure 12:
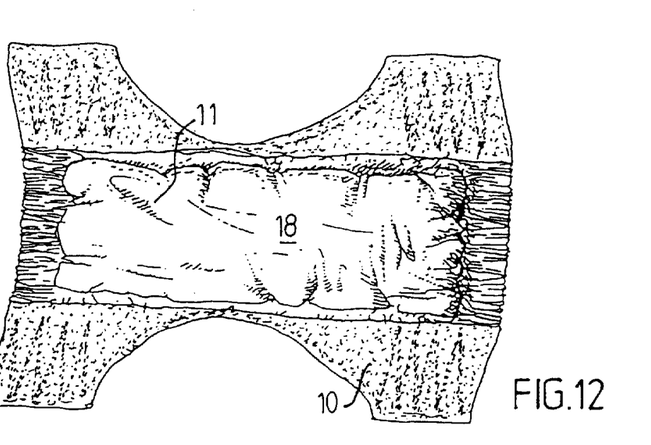
FIG. 12 is a pictorial representation of the pant substrate of FIG. 10 with an elastic pattern (not shown) with an absorption unit of a second embodiment fastened to the pant substrate.

In FIG. 12, an absorption unit 11 covers both the urine opening 14 and the anal opening 15. The absorption unit 11 may comprise absorbent material inside a cover 16.

The absorbent articles according to FIG. 11 and 12 can be modified. The important thing is, in contrast to known absorbent articles that a pant is formed which pant is in close contact with the user's skin all over the pant and proximate the user's urethral opening and anus and that the absorption unit is arranged on the outside of the pant and is held up by it.

The elastic pant can be designed with small holes 14, 15 because they are held in place and kept open by the elastic properties of the pant.

When feces or urine is excreted, they will pass through their respective holes and into their respective pockets in the absorption unit.

The urine and feces collecting parts 12, 13 can be fastened to the pant tightly sealed to the portions of the elastic pant immediately surrounding the respective ones of said holes.

The front pocket, absorption part, 12 may be filled and weighted down with urine without it pulling the elastic pant out of position in contact with the user. Since the two parts 12 and 13 are separated from each other the feces and urine will not mix, which is advantageous for preventing irritation to the skin.

The cover 16 and 17 can be made of elastic material to be able to expand as they are filled with feces or urine. The covers 17 and 18 can also be folded as a bellows to expand as they are filled.

What is claimed is:

1. A method of applying thread to a moving substrate web for making a disposable absorbent product having two waist portions and an intervening crotch portion, the method comprising the steps of:

rotating peripheries of two elements, which are inclined towards each other, through a first position where the two rotating peripheries are closest and a second position where the two rotating peripheries are farthest apart, each of the two rotating peripheries having plural elements projecting therefrom that pass through the first and second positions as the two peripheries rotate, one of the rotating peripheries having at least two of the projecting elements pass through the first position consecutively before one of the projecting elements from the other of the rotating peripheries passes through the first position;

moving the substrate web relative to the second position;

directing a thread to the first position and engaging the thread sequentially with each of the plural projecting elements as the plural projecting elements pass through the first position;

routing respective first portions of the thread laterally across the substrate web at each of the two waist portions by movement away from the first position of a pair of the projecting elements, one from each of the two rotating peripheries, that engage ends of the respective first portions of the thread;

routing a second portion of the thread longitudinally on the substrate web through the crotch portion by movement away from the first position of the at least two projecting elements on the one of the rotating peripheries, the at least two projecting elements engaging ends of the second portion of the thread; and transferring and fixing said first and second thread portions to the moving substrate web.

2. A device for applying a thread to a moving substrate web, comprising:

two elements inclined towards each other so that they define a first position where said two elements are closest and a second position where said two elements are farthest apart, each of said two elements having a rotating periphery with plural elements projecting therefrom that pass through the first and second positions as said rotating peripheries rotate, one of said rotating peripheries having at least two of said projecting elements pass through the first position consecutively before one of said projecting elements from the other of said rotating peripheries passes through the first position when said rotating peripheries rotate;

a substrate web for making a disposable absorbent product having two waist portions and an intervening crotch portion that moves relative to the second position;

a guide that directs a thread to the first position where the thread sequentially engages each of said projecting elements as said projecting elements pass through the first position when said rotating peripheries rotate;

a pair of said projecting elements, one from each of said rotating peripheries, engaging ends of respective first portions of the thread and routing the respective first portions of the thread laterally across each of said two waist portions by movement of said pair of projecting elements away from the first position; and said at least two of said projecting elements routing a second portion of the thread longitudinally on said crotch portion by movement away from the first position of said at least two projecting elements, said at least two projecting elements engaging ends of the second portion of the thread; and means for transferring and fixing said first and second portions of the thread to said product.

\* \* \* \* \*